(12) United States Patent
Scott

(10) Patent No.: US 6,368,790 B1
(45) Date of Patent: Apr. 9, 2002

(54) CDNA ENCODING P2P PROTEINS AND USE OF P2P CDNA DERIVED ANTIBODIES AND ANTISENSE REAGENTS IN DETERMINING THE PROLIFERATIVE POTENTIAL OF NORMAL, ABNORMAL, AND CANCER CELLS IN ANIMALS AND HUMANS

(75) Inventor: Robert E. Scott, Memphis, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 08/801,308

(22) Filed: Feb. 18, 1997

Related U.S. Application Data

(60) Provisional application No. 60/027,568, filed on Sep. 27, 1996.

(51) Int. Cl.[7] .......................... C12Q 1/68; C12N 15/12
(52) U.S. Cl. ...................... 435/6; 536/23.5; 536/24.5
(58) Field of Search ............................. 536/23.5, 24.5

(56) References Cited

PUBLICATIONS

Uhlmann et al. Antisense Oligonucleotides: A New Therapeutic Principle. Chemical Reviews 542–584 (vol. 90, No. 4, Jun. 1990.*
Milner et al. Selecting effective antisense reagents on combinatorial oligonucleotide arrays, Nature Biotechnology vol. 15 pages 637–541, 1997.
Elkind NB; Goldfinger N; Rotter V; Spot–1, a novel NLS–binding protein that interacts with p53 through a domain encoded by p(CA)n repeats; Oncogene (England), Sep. 7, 1995, 11(5) p. 841–51.
Sakai, Y. et al, cDNA Sequence and Chromosomal Localization of a Novel Human Protein, RBQ (RBBP6), that Binds to the Retinoblastoma Gene Product, Genomes, 30, pp. 98–101 (1995).
Ozaki, T., et al., Complex formation between lamin A and the retinoblastomagene product: identification of the domain on lamin A required for its interaction, Oncogene, 1994, 9, 2649–2653.
Studier, F. W., et al., Use of Bacteriophage T7 RNA Polymerase to Direct Selective High–level Expression of Cloned Genes, J. Mol. Biol., 1986, 189, 113–130.
Durfee, T., et al., The Amino–terminal Region of the Retinoblastoma Gene Product Binds a Novel Nuclear Matrix Protein That Co–Localizes to Centers for RNA Processing, Journal of Cell Biology, 1994, 127, 609–622.
Tontonoz, P., et al., Stimulation of Adipogenesis in Fibroblasts by PPARγ2, a Lipid–Activated Transcription Factor, Cell, 1994, 79, 1147–1156.
Wier, M. L., et al., Aproliferin–A Human Plasma Protein That Induces the Irreversible Loss of Proliferative Potential Associated With Terminal Differentiation, AJP, vol. 3, No. 3, 1986, 546–554.

Witte, M. M., et al., Repression of Two Proliferation Proteins during Senescence and Terminal Differentiation in Normal or SV40 Transfected Human Keratinocytes: P2Ps and SV40 Large T Antigen, Molecular and Cellular Differentiation, 1993, 1(2), 185–195.
Larsson, S. H., et al., Subnuclear Localization of WT1 in Splicing or Transcription Factor Domains Is Regulated by Alternative Splicing, Cell, 1995, 81, 391–401.
Freemont, P. S., et al., A Novel Cysteine–Rich Sequence Motif, Cell, 1991, 64, 483–484.
Paggi, M. G., et al., Defective Human Retinoblastoma Protein Identified by Lack of Interaction with the EIA Oncoprotein[1], Cancer Research, 1994, 54, 1098–1104.
Minoo, P., et al., Loss of Proliferative Potential during Terminal Differentiation Coincides with the Decreased Abundance of a Subset of Heterogeneous Ribonuclear Proteins, Journal of Cell Biology, 1989, 109, 1937–1946.
Scott, R. E., et al., Coupling of Proadipocyte Growth Arrest and Differentiation. II. A Cell Cycle Model for the Physiological Control Proliferation, Journal of Cell Biology, 1982, 94, 400–405.
Berg, J. M., et al., The Galvanization of Biology: A Growing Appreciation for the Roles of Zinc, Science, 1996, 271, 1081–1085.
Dacheng He, et al., Localization of heterogeneous nuclear ribonucleoprotein in the interphase nuclear matrix core filaments and on perichromosomalfilaments at mitosis,Proc. Natl. Acad. Sci. USA, 1991, 88, 7469–7473.
Smyth, M. J., Proadipocyte cell lines: models of cellular proliferation and differentation, Journal of Cell Science, 1993, 106, 1–9.
Smas, C. M., et al., Control of adipocyte differentiation, Biochem. J., 1995, 309, 697–710.
Dreyfuss, G., et al., hnRNP Proteins and the Biogenesis of mRNA, Annu. Rev. Biochem, 1993, 62:289–321.
Lester, G. P., et al., Monoclonal Antibodies to hnRNP, supplementary information,J. Biol. Chem., 1984, 259, 1833.

* cited by examiner

Primary Examiner—John S. Brusca
(74) Attorney, Agent, or Firm—Benjamin Aaron Adler

(57) ABSTRACT

Terminal differentiation is associated with repression in the expression of the P2P subset of hnRNP proteins. The present invention provides a P2P cDNA that encodes proteins with domains for hnRNP association and Rb1 binding. Probes to the P2P cDNA detect a single 8 kb mRNA in multiple murine tissues, in proliferating murine 3T3 cells but not in terminally differentiated 3T3T adipocytes. The interaction of P2P cDNA products and Rb1 may serve to modulate cell proliferation and/or other biological functions associated with tumor suppression by an RNA processing mechanism. Moreover, it was shown that P2P antisense oligonucleotides selectively repressed 30–40 kDa P2P expression.

19 Claims, 11 Drawing Sheets

MMEVKDPNMKGAMLTNTGKYAIPTIDAEAYAIGKKEKPPFLPEEPSSSEEDDPIPAELL 60
CLICKDIMTDAVVIPCCGNSSCDECIRTTLLESDKHTCPTCHQNDVSPDALIANKFLRQA 120
VNNFKNETGYTKRLRKQLPPFLFLVPPPRPLSQRNLQPRSRSPILRQQDPVVFRYTVSPT 180
CSDTKTAGSCSDSGTLSRLPAPSISSLTSNQSSLAPPVSGNPSSAPAPVPDITATVSISV 240
HSEKSDGPFRDSDNKLLPAAALTSEHSKGASSIAITALMEEKGVPGTSPWNSIFVGQSLL 300
HGQLIPTTGPVRINAARPGGGRPGWEHSNKLGYLVSPPQQIRRGERSCYRSINRGRHHSE 360
RSQRTQSPSLPATPCFVPPPLYPPPPHTLPLPPGVPPPQFPSSQPPTAGYSVP 420
PPGFPPAPANISTACFSPGVPTAHSNTMPTTQAPLLSREEFYREQNDKGRESKFPYSGSS 480
YSRSSYTDSSQGLAQHIHALTLSPSAAHTLDLLHDHPHPPEEAEARSAMIVHMPDLMDIA 540
HARSRSPPYRYRSRSRSPPEFRGQSPTKRNVPREEKEREYFNRYREVPPPYDIKAYYGR 600
SVDFRDPFEKERYREWERKYREWYEKYYKGYAVGAQPRPSANREDFSPERLLPLNIRNSP 660
FTRGRREDYAAGQSHRNRNLGGNYPEKLSTRDSHNAKDNPKSKEKESENVPGDGKGNKHK 720
KHRKRRNEEKGEESESFLNPELLETSRKCRGSSGIDETKTDTLFVLPSRDDATPVRDEPM 780
DAESITFKSVSDKDKREKDKPKVKSDKTKRKSDGSATAKKDNVLKPSKGPQEKVDGDREK 840
SPRSEPPLKKAKEEATKIDSVKPSSSSQKDEKVTGTPRKAHSKSAKDTRRQSQPRTRRSK 900
RTVPKTSSQKSQPVRTRRPRSLRKINYLIAREKNEREKRKKSVDKDFESSSMKISKVEGT 960
EIVKPSPKRKMEGDVEKLERTPEKDKIASSTTPAKKIKLNRETGKKIGNAENASTTKEPS 1020
EKLESTSSKIKQEKVKGKAKRKVAGSEGSSTLVDYTSTSSTGGSPVRKSEEKTDTKRTV 1080
IKTMEEYNNDNTAPAEDVIMIQVPQSKWDKDDEESEEDVKTTQPIQSVGKPSSIIKNV 1140
TTKPSATAKYTEKESEQPEKLQKLPKEASHELMQHELRSSKGSASSEKGRAKDREHSGSE 1200
KDNPDKRKSGAQPDKESTVDRLSEQGHFKTLSQSSKETRTSEKHESVRGSSNKDFTPGRD 1260
KKVDYDSRDYSSSKRRDERGELARRKDSPPRGKESLSGQKSKLREERDLPKKGAESKKSN 1320
SSPPRDKKPHDHKAPYETKRPCEETKPVDKNSGKEREKHAAEAARNGKESSGANCHVYLTR 1380
QTLPWRRSWLLGRWRRAPSSRNPS 1404

Fig. 2

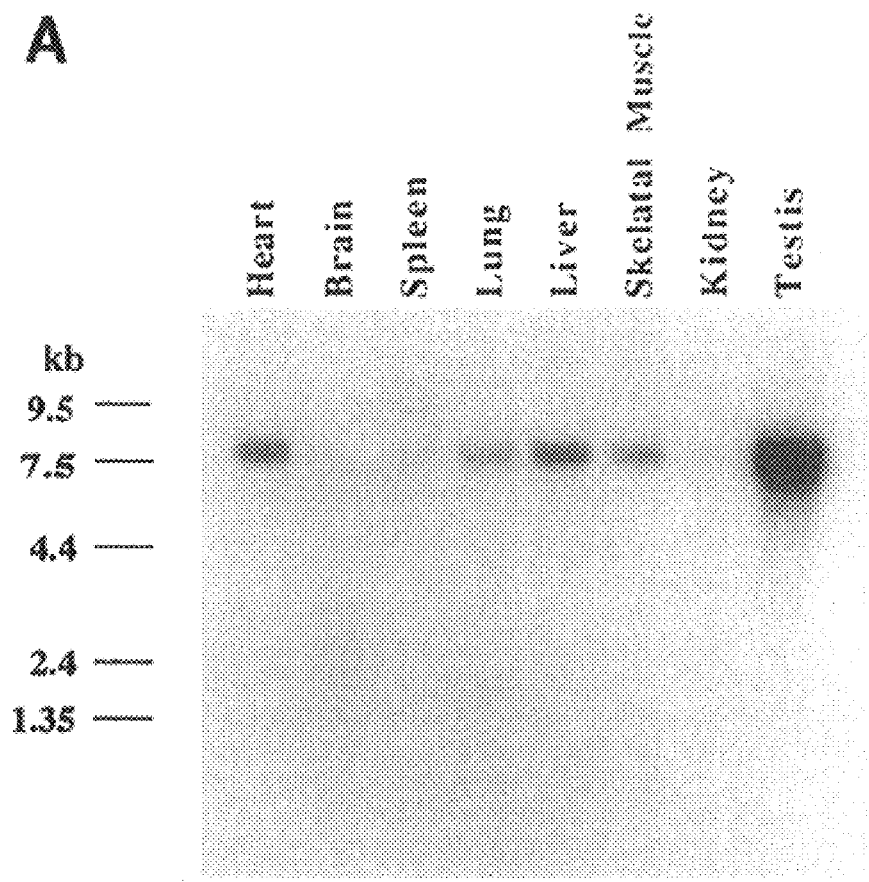
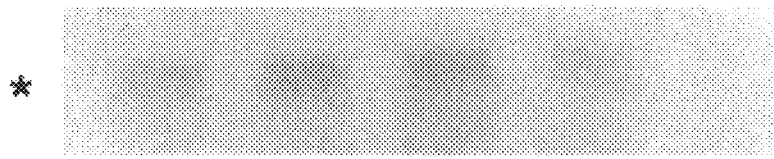
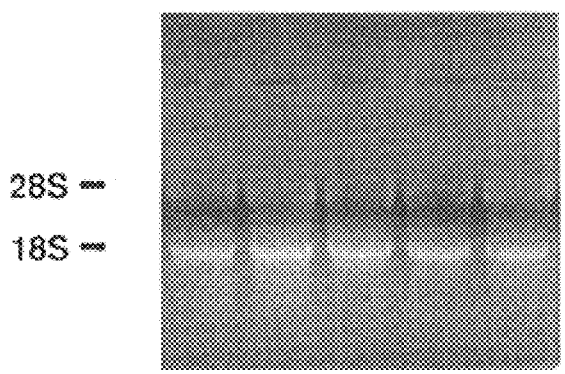
Fig. 3

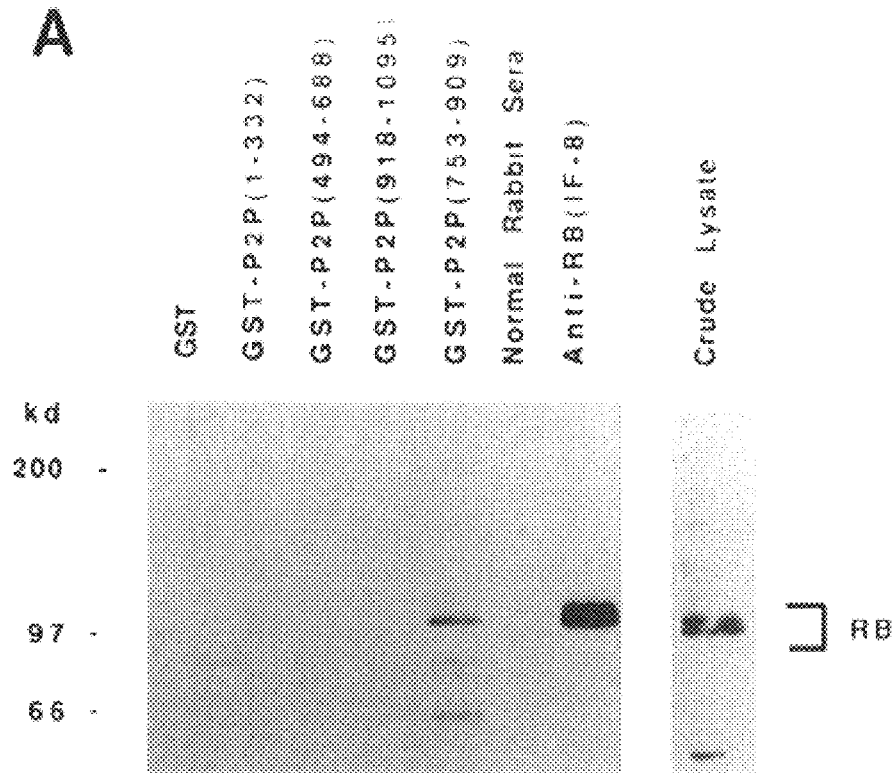
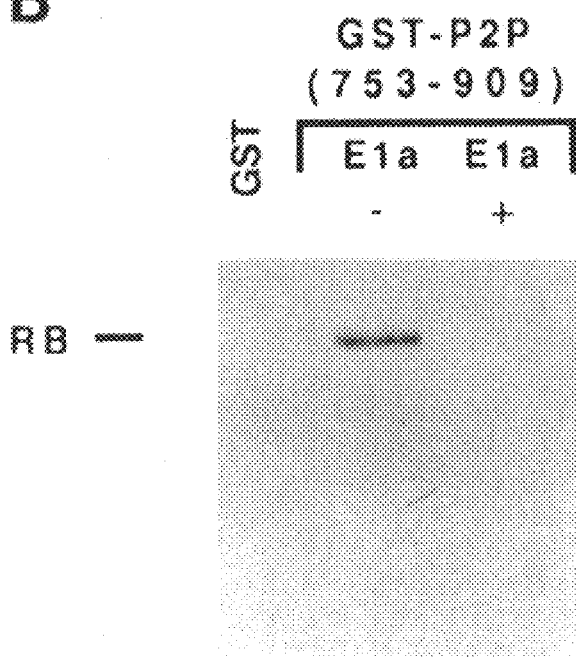
Fig. 5

```
                                                           60
                                                           *
AGGTCCACCACCTCCATCTTACACCTGCTTTCGTTGTGGTAAACCTGGTCATTATATTAAGAAT
                                                          120
                                                           *
TGCCAACAAATGGGGATAAGAACTTTGAATCTGGTCCTAGGATCAAAAAGAGCACTGGAATTCC
                                                          180
                                                           *
TAGAAGTTTTATGATGGAAGTGAAAGATCCTAACATGAAAGGTGCAATGCTTACCAACACTGGA
                                                          240
                                                           *
AAATATGCAATACCAACTATAGATGCAGAGGCCTATGCAATCGGGAAGAAAGAGAAACCACCCT
                                                          300
                                                           *
TCTTACCAGAGGAGCCATCATCATCTTCAGAAGAAGATGATCCTATCCCAGCAGAGCTCTTGTG
                                                          360
                                                           *
CCTCATCTGCAAAGACATCATGACTGATGCTGTGGTCATTCCCTGCTGTGGAAACAGTTCATGT
                                                          420
                                                           *
GATGAATGTATAAGAACGACACTCTTGGAGTCAGATAAACATACATGTCCAACATGTCACCAAA
                                                          480
                                                           *
ATGATGTTTCTCCTGATGCTTTAATTGCCAACAAGTTTTTACGACAGGCTGTTAATAACTTTAA
                                                          540
                                                           *
AAATGAAACTGGCTATACAAAACGACTACGAAAACAGTTACCTCCATTTTTATTTTTAGTACCA
                                                          600
                                                           *
CCACCAAGACCACTCAGTCAGCGGAACCTACAGCCTCGTAGTAGATCTCCAATACTAAGACAGC
                                                          660
                                                           *
AGGATCCTGTAGTATTCAGGTACACTGTCTCGCCTACCTGCTCCGATACTAAGACAGCAGGATC
                                                          720
                                                           *
CTGTAGTGATTCAGGTACACTGTCTCGCCTACCTGCTCCGTCTATATCTTCATTAACTTCTAAT
                                                          780
                                                           *
CAGTCTTCCTTGGCCCCTCCTGTGTCTGGAAATCCGTCTTCTGCTCCAGCTCCAGTACCTGATA
                                                          840
                                                           *
TAACTGCAACCGTGTCTATATCAGTCCACTCAGAAAAATCGGATGGACCTTTTCGGGATTCTGA
900                                                       960
 *                                                         *
TAATAAATTATTGCCAGCTGCCGCCCTTACATCAGAACATTCAAAGGGAGCCTCTTCAATTGCT
                                                         1020
                                                           *
ATTACTGCTCTTATGGAAGAAAAAGGGGTACCAGGTACCAGTCCTTGGAACTCCATCTTTGTTG
```

Fig. 6A

```
                                                                1080
                                                                  *
GACAGTCATTATTACATGGACAGTTGATTCCCACAACTGGCCCAGTAAGAATCAATGCTGCTCG
                                                1140
                                                  *
TCCAGGTGGTGGCCGGCCAGGCTGGGAGCATTCCAACAAGCTTGGGTACCTAGTTTCTCCACCA
                          1200
                            *
CAGCAAATTAGAAGAGGAGAAAGAAGCTGTTACAGAAGTATAAACCGCGGGCGACACCACAGCG
                                    1260
                                      *
AACGATCACAGAGGACTCAAAGCCCATCACTTCCAGCAACTCCATGCTTTGTGCCCGTTCCACC
                              1320
                                *
ACCTCCTTTGTATCCGCCTCCTCCCCATACACTTCCTCTTCCTCCAGGTGTACCTCCTCCACAG
                      1380
                        *
TTTTCTCCTCAGTTTCCCTCCTCCCAGCCTCCAACAGCAGGATATAGTGTCCCTCCTCCAGGAT
                            1440
                              *
TTCCACCAGCTCCTGCCAATATATCAACAGCTTGCTTTTCACCAGGTGTTCCCACTGCCCATTC
                  1500
                    *
AAATACCATGCCCACAACACAAGCACCTCTTTTGTCCAGGGAAGAATTCTATAGAGAGCAAAAC
                1560
                  *
GACAAAGGAAGAGAGTCTAAATTTCCCTATAGTGGGTCATCGTATTCAAGAAGTTCATACACTG
              1620
                *
ACTCAAGTCAAGGTCTGGCTCAACACATTCACGCTCTTACTCTCAGTCCTTCAGCTGCTCACAC
            1680
              *
TCTCGATCTTCTTCACGATCATCCCCATCCTCCAGAAGAGGCAGAGGCAAGATCTGCAATGATT
        1740
          *
GTTCACATGCCAGATCTCATGGATATCGCCCATGCTAGGTCAAGGTCACCTCCCTATAGACGAT
      1800
        *
ATCGCTCACGGTCCAGATCTCCTCCAGAATTTAGGGGACAGTCTCCCACTAAACGTAATGTACC
1860                                                            1920
  *                                                               *
TCGAGAAGAGAAAGAACGTGAGTATTTTAATAGATACAGAGAAGTTCCACCCCCTTATGACATC
                                              1980
                                                *
AAAGCCTATTATGGGCGGAGTGTCGACTTTAGAGACCCATTTGAGAAAGAACGCTACCGGGAAT
                                      2040
                                        *
GGGAAAGGAAATACCGAGAGTGGTATGAGAAGTACTACAAAGGGTACGCGGTGGGAGCTCAACC
```

Fig. 6B

```
                                                      2100
                                                       *
TAGACCCTCAGCCAATAGAGAGGACTTTTCTCCAGAGAGACTCTTACCTCTTAATATCAGAAAT
                              2160
                               *
TCACCCTTCACAAGAGGCCGCAGAGAAGACTATGCTGCTGGACAAAGTCATAGAAATAGAAATC
                              2220
                               *
TAGGTGGCAACTATCCAGAAAAGCTTTCAACAAGGGACAGTCACAATGCAAAAGATAATCCAAA
                              2280
                               *
ATCGAAGGAGAAGGAGAGTGAGAATGTTCCAGGAGACGGCAAAGGGAACAAGCATAAGAAACAC
                              2340
                               *
AGGAAACGAAGAAACGAAGAAAAGGGGGAAGAGAGTGAGAGCTTCCTGAACCCAGAGCTACTGG
                              2400
                               *
AGACGTCTAGGAAATGCAGGGGATCGTCAGGGATTGATGAAACGAAGACAGATACACTGTTTGT
                              2460
                               *
TCTCCCAAGCAGAGACGATGCTACACCTGTTAGGGATGAGCCAATGGACGCAGAATCGATCACT
                              2520
                               *
TTCAAGTCAGTATCTGACAAAGACAAGAGGGAAAAGGATAAGCCAAAAGTAAAAAGTGACAAGA
                              2580
                               *
CCAAACGGAAAAGTGACGGGTCTGCTACAGCCAAGAAAGACAATGTTTTAAAACCTTCTAAAGG
                              2640
                               *
ACCTCAAGAAAAGGTAGATGGAGACCGTGAAAAGTCTCCTCGGTCTGAGCCGCCACTCAAAAAA
                              2700
                               *
GCCAAAGAGGAGGCTACAAAGATTGACTCTGTAAAACCTTCCTCGTCTTCTCAGAAGGATGAGA
                              2760
                               *
AGGTCACTGGAACCCCTAGAAAAGCCCATTCTAAATCTGCAAAAGACACCAGGAGGCAAAGCCA
2820                                                            2880
 *                                                               *
GCCAAGGACGAGAAGGTCAAAAAGGACTGTTCCAAAGACATCAAGTCAGAAAAGCCAGCCAGTA
                              2940
                               *
AGGACGAGAAGGCCAAGAAGCCTGAGAAAAATAAACTACTTGATAGCAAGGGAGAAAAACGAAA
                              3000
                               *
GAGAAAAACGGAAGAAGAGTGTAGATAAAGATTTTGAGTCGTCTTCAATGAAAATCTCTAAAGT
```

Fig. 6C

```
                                    3060
                                     *
AGAAGGAACAGAAATAGTGAAACCATCACCAAAACGGAAAATGGAAGGTGATGTTGAAAAGCTG
                          3120
                           *
GAAAGGACCCCAGAAAAGGACAAGATTGCATCATCAACTACTCCAGCCAAAAAAATCAAACTCA
                     3180
                      *
ACAGAGAAACTGGAAAAAAAATTGGAAATGCAGAAAATGCATCTACTACAAAAGAACCCTCTGA
                          3240
                           *
AAAATTGGAGTCAACATCTAGCAAAATCAAACAGGAAAAAGTCAAGGGAAAGGCCAAACGGAAA
                   3300
                    *
GTAGCTGGGTCGGAAGGCTCCAGCTCCACGCTTGTGGATTACACCAGTACAAGTTCAACTGGAG
                          3360
                           *
GCAGTCCTGTGAGGAAATCTGAAGAAAAGACAGATACAAAGCGAACAGTCATTAAAACTATGGA
                     3420
                      *
GGAATATAATAATGATAACACAGCTCCTGCTGAAGATGTTATAATTATGATCCAGGTTCCTCAG
                     3480
                      *
TCCAAATGGGATAAAGATGACTTTGAGTCTGAAGAAGAAGATGTTAAAACCACACAACCTATAC
                 3540
                  *
AGAGTGTAGGGAAACCATCGAGTATTATAAAAAATGTCACTACTAAGCCATCGGCTACGGCTAA
                 3600
                  *
GTACACCGAGAAGGAAAGCGAGCAGCCCGAGAAACTGCAGAAGCTTCCCAAGGAGGCGAGCCAC
              3660
               *
GAGCTGATGCAGCACGAGCTCAGGAGCTCAAAGGGCAGTGCGTCCAGTGAGAAGGGCAGAGCCA
                3720
                 *
AGGACCGGGAGCACTCAGGGTCGGAGAAGGACAACCCTGACAAGAGGAAGAGCGGTGCCCAGCC
3780                                                        3840
 *                                                            *
AGACAAGGAGAGCACTGTGGACCGCCTGAGTGAGCAGGGACATTTTAAGACTCTCTCTCAGTCT
                                                   3900
                                                    *
TCCAAAGAGACCAGGACTTCAGAGAAGCACGAGTCTGTTCGTGGTTCCTCAAATAAAGACTTCA
                                   3960
                                    *
CTCCTGGTAGAGACAAGAAAGTGGACTACGACAGCAGGGATTATTCCAGTTCCAAGCGAAGAGA
                                          4020
                                           *
CGAGAGAGGTGAATTAGCAAGGAGAAAAGACTCTCCTCCCCGGGGCAAAGAGTCTCTGTCTGGG
```

Fig. 6D

```
                                        4080
                                          *
CAGAAAAGCAAGCTGAGGGAGGAGAGAGATTTACCTAAAAAGGGGGCCGAGTCAAAAAAAGTA
                                4140
                                  *
ATTCTAGCCCCCCAAGAGACAAAAAGCCTCATGATCATAAAGCCCCCTACGAAACTAAACGCCC
                                        4200
                                          *
ATGTGAAGAGACAAAGCCTGTAGATAAAAACTCTGGGAAGGAGCGGGAGAAGCATGCTGCTGAA
                                4260
                                  *
GCTCGCAATGGGAAAGAGTCCAGTGGTGCAAACTGCCATGTATACCTAACCCGCCAGACCCTCC
                                4320
                                  *
CATGGAGAAGGAGCTGGCTGCTGGGCAGGTGGAGAAGAGCGCCGTCAAGCCGAAACCCCAGCTG
                        4380
                          *
AGCCATTCCTCGAGGCTTTCCTCTGACCTGACCCGGGAGACGAACGAGGCAGCCTTTGAACCAG
                        4440
                          *
ATTATAATGAGAGCGACAGTGAGAGTAATGTGTCTGTGAAGGAAGAAGAAGCTGTTGCCAGTAT
                                4500
                                  *
CTCCAAGGACTTGAAAGAGAAAACAACAGAGAAAGCGAAAGAGAGCTTGACTGTAGCAACGGCC
                        4560
                          *
AGCCAGCCAGGTGCAGACAGGAGCCAGAGCCAAAGTAGCCCAGTGTTAGTCAGTAGAGTCATAG
                        4620
                          *
CCTTCGGAGCCAGACCCGAAGCCACAGCAGCAGTGCCAGCTCAGCCGGAAGGCCAGGACAGCAA
                4680
                  *
AAAGAAGAAGAAGAAGGAGAAGAAAAACGACAAGAAGCATAAAAAGCACAAGAAGCACAAG
4740                                                                4800
  *                                                                   *
AAGCACGCAGGCCGACGGCGACGTGGAGAAGAGCCAGAAACACAAACACAAGAAGAAGAAGGCC
                                                                4860
                                                                  *
AAGAAGAACAAAGACAAGGAGAAGGAGAAAGATGACCAAAAAGTGAGATCTGTCACTGTGTGAA
                                        4920
                                          *
GGACGGATGTGTTAATTGACTTAATTACTAAGTCATCTGTATTAAATTCTGTTATAATGTAAAG
                                4980
                                  *
AGATTCCAGCCTTGTAAATAATGAATGGAAGACCCTGTGCTGCACTTAAAAGTATTTGCTGCTT
                                        5040
                                          *
GATTATTTCATTTTTACATCAGAGCTTTATAACGAACTTTTGTACAGAATTGTGAGTTGTGACC
```

Fig. 6E

```
                                    5100
                                     *
ATGGAACAGTGAGAGGTTTTGCTAGGGCCTATTATTTTTAACCACCATTAATTAGTTGGGGTGG
                              5160
                               *
AGTTTACTGTACTGTGAAATTTTCACATTTGAATTTTTTTAATTGCCTGGCAA
```

Fig. 6F

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1404 amino acids
      (B) TYPE: amino acid
      (D) TOPOLOGY: linear (ii) MOLECULE TYPE: protein (xi) SEQUENCE DESCRIPTION: SEQ ID NO:1:

```
Met Met Glu Val Lys Asp Pro Asn Met Lys Gly Ala Met Leu Thr Asn
1               5                   10                  15

Thr Gly Lys Tyr Ala Ile Pro Thr Ile Asp Ala Glu Ala Tyr Ala Ile
            20                  25                  30

Gly Lys Lys Glu Lys Pro Pro Phe Leu Pro Glu Glu Pro Ser Ser Ser
        35                  40                  45

Ser Glu Glu Asp Asp Pro Ile Pro Ala Glu Leu Leu Cys Leu Ile Cys
    50                  55                  60

Lys Asp Ile Met Thr Asp Ala Val Val Ile Pro Cys Cys Gly Asn Ser
```

-continued

```
 65                     70                      75                      80
Ser Cys Asp Glu Cys Ile Arg Thr Thr Leu Leu Ser Asp Lys His
                    85                      90                      95

Thr Cys Pro Thr Cys His Gln Asn Asp Val Ser Pro Asp Ala Leu Ile
                   100                     105                     110

Ala Asn Lys Phe Leu Arg Gln Ala Val Asn Asn Phe Lys Asn Glu Thr
                   115                     120                     125

Gly Tyr Thr Lys Arg Leu Arg Lys Gln Leu Pro Pro Phe Leu Phe Leu
                   130                     135                     140

Val Pro Pro Arg Pro Leu Ser Gln Arg Asn Leu Gln Pro Arg Ser
145                     150                     155                     160

Arg Ser Pro Ile Leu Arg Gln Gln Asp Pro Val Val Phe Arg Tyr Thr
                   165                     170                     175

Val Ser Pro Thr Cys Ser Asp Thr Lys Thr Ala Gly Ser Cys Ser Asp
                   180                     185                     190

Ser Gly Thr Leu Ser Arg Leu Pro Ala Pro Ser Ile Ser Ser Leu Thr
                   195                     200                     205

Ser Asn Gln Ser Ser Leu Ala Pro Pro Val Ser Gly Asn Pro Ser Ser
                   210                     215                     220

Ala Pro Ala Pro Val Pro Asp Ile Thr Ala Thr Val Ser Ile Ser Val
225                     230                     235                     240

His Ser Glu Lys Ser Asp Gly Pro Phe Arg Asp Ser Asp Asn Lys Leu
                   245                     250                     255

Leu Pro Ala Ala Ala Leu Thr Ser Glu His Ser Lys Gly Ala Ser Ser
                   260                     265                     270

Ile Ala Ile Thr Ala Leu Met Glu Glu Lys Gly Val Pro Gly Thr Ser
                   275                     280                     285

Pro Trp Asn Ser Ile Phe Val Gly Gln Ser Leu Leu His Gly Gln Leu
                   290                     295                     300

Ile Pro Thr Thr Gly Pro Val Arg Ile Asn Ala Ala Arg Pro Gly Gly
305                     310                     315                     320

Gly Arg Pro Gly Trp Glu His Ser Asn Lys Leu Gly Tyr Leu Val Ser
                   325                     330                     335

Pro Pro Gln Gln Ile Arg Arg Gly Glu Arg Ser Cys Tyr Arg Ser Ile
                   340                     345                     350

Asn Arg Gly Arg His His Ser Glu Arg Ser Gln Arg Thr Gln Ser Pro
                   355                     360                     365

Ser Leu Pro Ala Thr Pro Cys Phe Val Pro Val Pro Pro Pro Leu
370                     375                     380

Tyr Pro Pro Pro His Thr Leu Pro Leu Pro Pro Gly Val Pro Pro
385                     390                     395                     400

Pro Gln Phe Ser Pro Gln Phe Pro Ser Ser Gln Pro Pro Thr Ala Gly
                   405                     410                     415

Tyr Ser Val Pro Pro Gly Phe Pro Pro Ala Pro Ala Asn Ile Ser
                   420                     425                     430

Thr Ala Cys Phe Ser Pro Gly Val Pro Thr Ala His Ser Asn Thr Met
                   435                     440                     445

Pro Thr Thr Gln Ala Pro Leu Leu Ser Arg Glu Glu Phe Tyr Arg Glu
                   450                     455                     460

Gln Asn Asp Lys Gly Arg Glu Ser Lys Phe Pro Tyr Ser Gly Ser Ser
465                     470                     475                     480

Tyr Ser Arg Ser Ser Tyr Thr Asp Ser Ser Gln Gly Leu Ala Gln His
                   485                     490                     495
```

-continued

```
Ile His Ala Leu Thr Leu Ser Pro Ser Ala Ala His Thr Leu Asp Leu
            500                 505                 510
Leu His Asp His Pro His Pro Pro Glu Glu Ala Glu Ala Arg Ser Ala
            515                 520                 525
Met Ile Val His Met Pro Asp Leu Met Asp Ile Ala His Ala Arg Ser
            530                 535                 540
Arg Ser Pro Pro Tyr Arg Arg Tyr Arg Ser Arg Ser Arg Ser Pro Pro
545                 550                 555                 560
Glu Phe Arg Gly Gln Ser Pro Thr Lys Arg Asn Val Pro Arg Glu Glu
                565                 570                 575
Lys Glu Arg Glu Tyr Phe Asn Arg Tyr Arg Glu Val Pro Pro Pro Tyr
            580                 585                 590
Asp Ile Lys Ala Tyr Tyr Gly Arg Ser Val Asp Phe Arg Asp Pro Phe
            595                 600                 605
Glu Lys Glu Arg Tyr Arg Glu Trp Glu Arg Lys Tyr Arg Glu Trp Tyr
            610                 615                 620
Glu Lys Tyr Tyr Lys Gly Tyr Ala Val Gly Ala Gln Pro Arg Pro Ser
625                 630                 635                 640
Ala Asn Arg Glu Asp Phe Ser Pro Glu Arg Leu Leu Pro Leu Asn Ile
                645                 650                 655
Arg Asn Ser Pro Phe Thr Arg Gly Arg Arg Glu Asp Tyr Ala Ala Gly
                660                 665                 670
Gln Ser His Arg Asn Arg Asn Leu Gly Gly Asn Tyr Pro Glu Lys Leu
            675                 680                 685
Ser Thr Arg Asp Ser His Asn Ala Lys Asp Asn Pro Lys Ser Lys Glu
            690                 695                 700
Lys Glu Ser Glu Asn Val Pro Gly Asp Gly Lys Gly Asn Lys His Lys
705                 710                 715                 720
Lys His Arg Lys Arg Arg Asn Glu Glu Lys Gly Glu Glu Ser Glu Ser
                725                 730                 735
Phe Leu Asn Pro Glu Leu Leu Glu Thr Ser Arg Lys Cys Arg Gly Ser
            740                 745                 750
Ser Gly Ile Asp Glu Thr Lys Thr Asp Thr Leu Phe Val Leu Pro Ser
            755                 760                 765
Arg Asp Asp Ala Thr Pro Val Arg Asp Glu Pro Met Asp Ala Glu Ser
770                 775                 780
Ile Thr Phe Lys Ser Val Ser Asp Lys Asp Lys Arg Glu Lys Asp Lys
785                 790                 795                 800
Pro Lys Val Lys Ser Asp Lys Thr Lys Arg Lys Ser Asp Gly Ser Ala
                805                 810                 815
Thr Ala Lys Lys Asp Asn Val Leu Lys Pro Ser Lys Gly Pro Gln Glu
            820                 825                 830
Lys Val Asp Gly Asp Arg Glu Lys Ser Pro Arg Ser Glu Pro Pro Leu
            835                 840                 845
Lys Lys Ala Lys Glu Glu Ala Thr Lys Ile Asp Ser Val Lys Pro Ser
            850                 855                 860
Ser Ser Ser Gln Lys Asp Glu Lys Val Thr Gly Thr Pro Arg Lys Ala
865                 870                 875                 880
His Ser Lys Ser Ala Lys Asp Thr Arg Arg Gln Ser Gln Pro Arg Thr
                885                 890                 895
Arg Arg Ser Lys Arg Thr Val Pro Lys Thr Ser Ser Gln Lys Ser Gln
            900                 905                 910
```

-continued

```
Pro Val Arg Thr Arg Arg Pro Arg Ser Leu Arg Lys Ile Asn Tyr Leu
        915                 920                 925

Ile Ala Arg Glu Lys Asn Glu Arg Glu Lys Arg Lys Lys Ser Val Asp
        930                 935                 940

Lys Asp Phe Glu Ser Ser Ser Met Lys Ile Ser Lys Val Glu Gly Thr
945                 950                 955                 960

Glu Ile Val Lys Pro Ser Pro Lys Arg Lys Met Glu Gly Asp Val Glu
                965                 970                 975

Lys Leu Glu Arg Thr Pro Glu Lys Asp Lys Ile Ala Ser Ser Thr Thr
            980                 985                 990

Pro Ala Lys Lys Ile Lys Leu Asn Arg Glu Thr Gly Lys Lys Ile Gly
            995                 1000                1005

Asn Ala Glu Asn Ala Ser Thr Thr Lys Glu Pro Ser Glu Lys Leu Glu
        1010                1015                1020

Ser Thr Ser Ser Lys Ile Lys Gln Glu Lys Val Lys Gly Lys Ala Lys
1025                1030                1035                1040

Arg Lys Val Ala Gly Ser Glu Gly Ser Ser Ser Thr Leu Val Asp Tyr
                1045                1050                1055

Thr Ser Thr Ser Ser Thr Gly Gly Ser Pro Val Arg Lys Ser Glu Glu
            1060                1065                1070

Lys Thr Asp Thr Lys Arg Thr Val Ile Lys Thr Met Glu Glu Tyr Asn
        1075                1080                1085

Asn Asp Asn Thr Ala Pro Ala Glu Asp Val Ile Ile Met Ile Gln Val
        1090                1095                1100

Pro Gln Ser Lys Trp Asp Lys Asp Phe Glu Ser Glu Glu Glu Asp
1105                1110                1115                1120

Val Lys Thr Thr Gln Pro Ile Gln Ser Val Gly Lys Pro Ser Ser Ile
                1125                1130                1135

Ile Lys Asn Val Thr Thr Lys Pro Ser Ala Thr Ala Lys Tyr Thr Glu
            1140                1145                1150

Lys Glu Ser Glu Gln Pro Glu Lys Leu Gln Lys Leu Pro Lys Glu Ala
            1155                1160                1165

Ser His Glu Leu Met Gln His Glu Leu Arg Ser Ser Lys Gly Ser Ala
        1170                1175                1180

Ser Ser Glu Lys Gly Arg Ala Lys Asp Arg Glu His Ser Gly Ser Glu
1185                1190                1195                1200

Lys Asp Asn Pro Asp Lys Arg Lys Ser Gly Ala Gln Pro Asp Lys Glu
                1205                1210                1215

Ser Thr Val Asp Arg Leu Ser Glu Gln Gly His Phe Lys Thr Leu Ser
            1220                1225                1230

Gln Ser Ser Lys Glu Thr Arg Thr Ser Glu Lys His Glu Ser Val Arg
        1235                1240                1245

Gly Ser Ser Asn Lys Asp Phe Thr Pro Gly Arg Asp Lys Lys Val Asp
        1250                1255                1260

Tyr Asp Ser Arg Asp Tyr Ser Ser Ser Lys Arg Arg Asp Glu Arg Gly
1265                1270                1275                1280

Glu Leu Ala Arg Arg Lys Asp Ser Pro Pro Arg Gly Lys Glu Ser Leu
                1285                1290                1295

Ser Gly Gln Lys Ser Lys Leu Arg Glu Glu Arg Asp Leu Pro Lys Lys
            1300                1305                1310

Gly Ala Glu Ser Lys Lys Ser Asn Ser Ser Pro Pro Arg Asp Lys Lys
        1315                1320                1325

Pro His Asp His Lys Ala Pro Tyr Glu Thr Lys Arg Pro Cys Glu Glu
```

```
                    1330              1335              1340
Thr Lys Pro Val Asp Lys Asn Ser Gly Lys Glu Arg Glu Lys His Ala
1345              1350              1355              1360

Ala Glu Ala Arg Asn Gly Lys Glu Ser Ser Gly Ala Asn Cys His Val
              1365              1370              1375

Tyr Leu Thr Arg Gln Thr Leu Pro Trp Arg Arg Ser Trp Leu Leu Gly
          1380              1385              1390

Arg Trp Arg Arg Ala Pro Ser Ser Arg Asn Pro Ser
      1395              1400
```

(2) INFORMATION FOR SEQ ID NO:2:

(i) SEQUENCE CHARACTERISTICS:
        (A) LENGTH: 5173 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
AGGTCCACCA CCTCCATCTT ACACCTGCTT TCGTTGTGGT AAACCTGGTC ATTATATTAA      60

GAATTGCCAA CAAATGGGGA TAAGAACTTT GAATCTGGTC CTAGGATCAA AAAGAGCACT     120

GGAATTCCTA GAAGTTTTAT GATGGAAGTG AAAGATCCTA ACATGAAAGG TGCAATGCTT     180

ACCAACACTG GAAAATATGC AATACCAACT ATAGATGCAG AGGCCTATGC AATCGGGAAG     240

AAAGAGAAAC CACCCTTCTT ACCAGAGGAG CCATCATCAT CTTCAGAAGA AGATGATCCT     300

ATCCCAGCAG AGCTCTTGTG CCTCATCTGC AAAGACATCA TGACTGATGC TGTGGTCATT     360

CCCTGCTGTG GAAACAGTTC ATGTGATGAA TGTATAAGAA CGACACTCTT GGAGTCAGAT     420

AAACATACAT GTCCAACATG TCACCAAAAT GATGTTTCTC CTGATGCTTT AATTGCCAAC     480

AAGTTTTTAC GACAGGCTGT TAATAACTTT AAAAATGAAA CTGGCTATAC AAAACGACTA     540

CGAAAACAGT TACCTCCATT TTTATTTTTA GTACCACCAC AAGACCACT CAGTCAGCGG      600

AACCTACAGC CTCGTAGTAG ATCTCCAATA CTAAGACAGC AGGATCCTGT AGTATTCAGG     660

TACACTGTCT CGCCTACCTG CTCCGATACT AAGACAGCAG GATCCTGTAG TGATTCAGGT     720

ACACTGTCTC GCCTACCTGC TCCGTCTATA TCTTCATTAA CTTCTAATCA GTCTTCCTTG     780

GCCCCTCCTG TGTCTGGAAA TCCGTCTTCT GCTCCAGCTC CAGTACCTGA TATAACTGCA     840

ACCGTGTCTA TATCAGTCCA CTCAGAAAAA TCGGATGGAC CTTTTCGGGA TTCTGATAAT     900

AAATTATTGC CAGCTGCCGC CCTTACATCA GAACATTCAA AGGGAGCCTC TTCAATTGCT     960

ATTACTGCTC TTATGGAAGA AAAAGGGGTA CCAGGTACCA GTCCTTGGAA CTCCATCTTT    1020

GTTGGACAGT CATTATTACA TGGACAGTTG ATTCCCACAA CTGGCCCAGT AAGAATCAAT    1080

GCTGCTCGTC CAGGTGGTGG CCGGCCAGGC TGGGAGCATT CCAACAAGCT TGGGTACCTA    1140

GTTTCTCCAC CACAGCAAAT TAGAAGAGGA GAAAGAAGCT GTTACAGAAG TATAAACCGC    1200

GGGCGACACC ACAGCGAACG ATCACAGAGG ACTCAAAGCC CATCACTTCC AGCAACTCCA    1260

TGCTTTGTGC CCGTTCCACC ACCTCCTTTG TATCCGCCTC CTCCCCATAC ACTTCCTCTT    1320

CCTCCAGGTG TACCTCCTCC ACAGTTTTCT CCTCAGTTTC CCTCCTCCCA GCCTCCAACA    1380

GCAGGATATA GTGTCCCTCC TCCAGGATTT CCACCAGCTC CTGCCAATAT ATCAACAGCT    1440

TGCTTTTCAC CAGGTGTTCC CACTGCCCAT TCAAATACCA TGCCCACAAC ACAAGCACCT    1500

CTTTTGTCCA GGGAAGAATT CTATAGAGAG CAAAACGACA AGGAAGAGA GTCTAAATTT     1560
```

```
CCCTATAGTG GGTCATCGTA TTCAAGAAGT TCATACACTG ACTCAAGTCA AGGTCTGGCT    1620

CAACACATTC ACGCTCTTAC TCTCAGTCCT TCAGCTGCTC ACACTCTCGA TCTTCTTCAC    1680

GATCATCCCC ATCCTCCAGA AGAGGCAGAG GCAAGATCTG CAATGATTGT TCACATGCCA    1740

GATCTCATGG ATATCGCCCA TGCTAGGTCA AGGTCACCTC CCTATAGACG ATATCGCTCA    1800

CGGTCCAGAT CTCCTCCAGA ATTTAGGGGA CAGTCTCCCA CTAAACGTAA TGTACCTCGA    1860

GAAGAGAAAG AACGTGAGTA TTTTAATAGA TACAGAGAAG TTCCACCCCC TTATGACATC    1920

AAAGCCTATT ATGGGCGGAG TGTCGACTTT AGAGACCCAT TTGAGAAAGA ACGCTACCGG    1980

GAATGGGAAA GGAAATACCG AGAGTGGTAT GAGAAGTACT ACAAAGGGTA CGCGGTGGGA    2040

GCTCAACCTA GACCCTCAGC CAATAGAGAG GACTTTTCTC CAGAGAGACT CTTACCTCTT    2100

AATATCAGAA ATTCACCCTT CACAAGAGGC CGCAGAGAAG ACTATGCTGC TGGACAAAGT    2160

CATAGAAATA GAAATCTAGG TGGCAACTAT CCAGAAAAGC TTTCAACAAG GACAGTCAC     2220

AATGCAAAAG ATAATCCAAA ATCGAAGGAG AAGGAGAGTG AGAATGTTCC AGGAGACGGC    2280

AAAGGGAACA AGCATAAGAA ACACAGGAAA CGAAGAAACG AAGAAAAGGG GGAAGAGAGT    2340

GAGAGCTTCC TGAACCCAGA GCTACTGGAG ACGTCTAGGA AATGCAGGGG ATCGTCAGGG    2400

ATTGATGAAA CGAAGACAGA TACACTGTTT GTTCTCCCAA GCAGAGACGA TGCTACACCT    2460

GTTAGGGATG AGCCAATGGA CGCAGAATCG ATCACTTTCA AGTCAGTATC TGACAAAGAC    2520

AAGAGGGAAA AGGATAAGCC AAAAGTAAAA AGTGACAAGA CCAAACGGAA AAGTGACGGG    2580

TCTGCTACAG CCAAGAAAGA CAATGTTTTA AAACCTTCTA AAGGACCTCA AGAAAAGGTA    2640

GATGGAGACC GTGAAAAGTC TCCTCGGTCT GAGCCGCCAC TCAAAAAAGC CAAAGAGGAG    2700

GCTACAAAGA TTGACTCTGT AAAACCTTCC TCGTCTTCTC AGAAGGATGA GAAGGTCACT    2760

GGAACCCCTA GAAAAGCCCA TTCTAAATCT GCAAAAGACA CCAGGAGGCA AGCCAGCCA    2820

AGGACGAGAA GGTCAAAAAG GACTGTTCCA AAGACATCAA GTCAGAAAAG CCAGCCAGTA    2880

AGGACGAGAA GGCCAAGAAG CCTGAGAAAA ATAAACTACT TGATAGCAAG GGAGAAAAAC    2940

GAAAGAGAAA AACGGAAGAA GAGTGTAGAT AAAGATTTTG AGTCGTCTTC AATGAAAATC    3000

TCTAAAGTAG AAGGAACAGA AATAGTGAAA CCATCACCAA AACGGAAAAT GGAAGGTGAT    3060

GTTGAAAAGC TGGAAAGGAC CCCAGAAAAG GACAAGATTG CATCATCAAC TACTCCAGCC    3120

AAAAAAATCA AACTCAACAG AGAAACTGGA AAAAAAATTG GAAATGCAGA AAATGCATCT    3180

ACTACAAAAG AACCCTCTGA AAAATTGGAG TCAACATCTA GCAAAATCAA ACAGGAAAAA    3240

GTCAAGGGAA AGGCCAAACG GAAAGTAGCT GGGTCGGAAG GCTCCAGCTC CACGCTTGTG    3300

GATTACACCA GTCAAGTTC AACTGGAGGC AGTCCTGTGA GGAAATCTGA AGAAAAGACA     3360

GATACAAAGC GAACAGTCAT TAAAACTATG GAGGAATATA ATAATGATAA CACAGCTCCT    3420

GCTGAAGATG TTATAATTAT GATCCAGGTT CCTCAGTCCA AATGGGATAA AGATGACTTT    3480

GAGTCTGAAG AAGAAGATGT TAAAACCACA CAACCTATAC AGAGTGTAGG GAAACCATCG    3540

AGTATTATAA AAAATGTCAC TACTAAGCCA TCGGCTACGG CTAAGTACAC CGAGAAGGAA    3600

AGCGAGCAGC CCGAGAAACT GCAGAAGCTT CCCAAGGAGG CGAGCCACGA GCTGATGCAG    3660

CACGAGCTCA GGAGCTCAAA GGGCAGTGCG TCCAGTGAGA AGGGCAGAGC CAAGGACCGG    3720

GAGCACTCAG GGTCGGAGAA GGACAACCCT GACAAGAGGA AGAGCGGTGC CCAGCCAGAC    3780

AAGGAGAGCA CTGTGGACCG CCTGAGTGAG CAGGGACATT TTAAGACTCT CTCTCAGTCT    3840

TCCAAAGAGA CCAGGACTTC AGAGAAGCAC GAGTCTGTTC GTGGTTCCTC AAATAAAGAC    3900

TTCACTCCTG GTAGAGACAA GAAAGTGGAC TACGACAGCA GGGATTATTC CAGTTCCAAG    3960
```

```
-continued

CGAAGAGACG AGAGAGGTGA ATTAGCAAGG AGAAAAGACT CTCCTCCCCG GGGCAAAGAG      4020

TCTCTGTCTG GGCAGAAAAG CAAGCTGAGG GAGGAGAGAG ATTTACCTAA AAAGGGGGCC      4080

GAGTCAAAAA AAAGTAATTC TAGCCCCCCA AGAGACAAAA AGCCTCATGA TCATAAAGCC      4140

CCCTACGAAA CTAAACGCCC ATGTGAAGAG ACAAAGCCTG TAGATAAAAA CTCTGGGAAG      4200

GAGCGGGAGA AGCATGCTGC TGAAGCTCGC AATGGGAAAG AGTCCAGTGG TGCAAACTGC      4260

CATGTATACC TAACCCGCCA GACCCTCCCA TGGAGAAGGA GCTGGCTGCT GGGCAGGTGG      4320

AGAAGAGCGC CGTCAAGCCG AAACCCCAGC TGAGCCATTC CTCGAGGCTT TCCTCTGACC      4380

TGACCCGGGA GACGAACGAG GCAGCCTTTG AACCAGATTA TAATGAGAGC GACAGTGAGA      4440

GTAATGTGTC TGTGAAGGAA GAAGAAGCTG TTGCCAGTAT CTCCAAGGAC TTGAAAGAGA      4500

AAACAACAGA GAAAGCGAAA GAGAGCTTGA CTGTAGCAAC GGCCAGCCAG CCAGGTGCAG      4560

ACAGGAGCCA GAGCCAAAGT AGCCCAGTGT TAGTCAGTAG AGTCATAGCC TTCGGAGCCA      4620

GACCCGAAGC CACAGCAGCA GTGCCAGCTC AGCCGGAAGG CCAGGACAGC AAAAAGAAGA      4680

AGAAGAAGAA GGAGAAGAAA AACGACAAGA AGCATAAAAA GCACAAGAAG CACAAGAAGC      4740

ACGCAGGCCG ACGGCGACGT GGAGAAGAGC CAGAAACACA AACACAAGAA GAAGAAGGCC      4800

AAGAAGAACA AAGACAAGGA GAAGGAGAAA GATGACCAAA AAGTGAGATC TGTCACTGTG      4860

TGAAGGACGG ATGTGTTAAT TGACTTAATT ACTAAGTCAT CTGTATTAAA TTCTGTTATA      4920

ATGTAAAGAG ATTCCAGCCT TGTAAATAAT GAATGGAAGA CCCTGTGCTG CACTTAAAAG      4980

TATTTGCTGC TTGATTATTT CATTTTTACA TCAGAGCTTT ATAACGAACT TTTGTACAGA      5040

ATTGTGAGTT GTGACCATGG AACAGTGAGA GGTTTTGCTA GGGCCTATTA TTTTTAACCA      5100

CCATTAATTA GTTGGGGTGG AGTTTACTGT ACTGTGAAAT TTTCACATTT GAATTTTTTT      5160

AATTGCCTGG CAA                                                        5173

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:3:

CAGCAGGAGC TGTGTT                                                     16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:4:

CTACTAAGCC ATCGGC                                                     16
```

CDNA ENCODING P2P PROTEINS AND USE OF P2P CDNA DERIVED ANTIBODIES AND ANTISENSE REAGENTS IN DETERMINING THE PROLIFERATIVE POTENTIAL OF NORMAL, ABNORMAL, AND CANCER CELLS IN ANIMALS AND HUMANS

This application claims the benefit of pending provisional application Ser. No. 60/027,568, filed Sep. 27, 1996.

BACKGROUND OF THE INVENTION

Differentiation in many cell lineages has been established to be a multistep process. This is perhaps best illustrated by analysis of the differentiation of 3T3T mesenchymal stem cells into adipocytes (1). Undifferentiated 3T3T cells first arrest their proliferation in the $G_1$ phase of the cell cycle at a distinct state prior to differentiation. Associated with this process, expression of the PPARα2 lineage specific transcription factor is induced (2). Thereafter, the C/EBP family of transcription factors is expressed to induce a series of adipocyte differentiation genes that include 422, GDPH, lipoprotein lipase and adipsin (3, 4, 5). The resultant adipocytes are nonterminally differentiated because they can be induced to reinitiate proliferation and reenter the cell cycle. Adipocytes at the nonterminal state of differentiation can however be induced to terminally differentiate by exposure to aproliferin and thereby irreversibly lose their growth factor responsiveness (6). When terminal adipocyte differentiation occurs a marked repression in the expression of P2P proteins is evident (7).

P2Ps, i.e. proliferation potential proteins, comprise a group of highly basic 35–40 kDa nuclear proteins that can bind to RNA and are associated with hnRNP particles as determined by sucrose gradient sedimentation of nuclear components (7). In this application, references to a singular P2P protein encompass the plural P2P "proteins", and vice versa. Antibodies prepared against core hnRNPs recognize P2Ps and 2D gel electrophoresis established that P2Ps are members of the A/B class of hnRNP proteins which are involved in RNA processing (7,9).

Terminal differentiation has also recently been demonstrated to require the expression of the tumor suppressor protein Rb1 (10). In studies using myoblasts derived from native animals that express Rb1 and myoblasts from transgenic animals that lack Rb1, it was established that cells lacking Rb1 cannot terminally differentiate. Instead, they are blocked at a state of nonterminal differentiation. These observations suggest that the function of Rb1 as a tumor suppressor gene product may be related to its role in the control of terminal differentiation. This possibility is supported by data showing that the Wilms' tumor suppressor gene product WT1 is also involved in the terminal differentiation of renal blastema cells during neonatal development (11). Recent reports also show that the Rb1 and WT1 proteins can be localized in the nucleus to sites of RNA processing suggesting that tumor suppressor mechanisms may be mediated by regulating the processing of specific mRNAs (12,13).

SUMMARY OF THE INVENTION

The invention is a novel P2P cDNA, the protein/proteins encoded by the P2P cDNA, monoclonal antibodies against P2P protein, a diagnostic method which involves detection of the DNA, an RNA transcribed by the DNA, or the protein, P2P antisense reagents derived from the P2P cDNA, and a method for gene therapy using these reagents.

The invention is partly based on evidence that the irreversible loss of proliferative potential is associated with repression in the expression of hnRNP-associated proteins that are involved in RNA processing which was published in 1989 (7). It was specifically demonstrated that the terminal differentiation of 3T3T adipocytes correlates with a markedly decreased expression of a set of proteins designated P2P, i.e. proliferation potential proteins, P2Ps were shown to have a pI of greater than 9.0, to range in size from 35 to 40 kDa and to localize to nuclear hnRNP particles as determined using sucrose gradient sedimentation methods. Additional studies established that P2Ps are recognized by the FA12 monoclonal antibody that detects purified core hnRNP proteins. The results of 2D gel electrophoresis further established that P2Ps are type A/B hnRNP proteins. P2Ps also share an epitope in common with hsp90 as determined by use of the AC88 monoclonal antibody even though P2Ps are not heat shock proteins. Subsequently, the terminal differentiation of human keratinocytes was also shown to be associated with a marked decrease in P2P expression (7) and P2P expression was shown to markedly decrease in association with the senescence of normal human cells (8). In contrast, it was shown that P2P expression is not repressed when malignant cells differentiate (7).

A description is provided of the cloning and characterization of the P2P cDNA. The result of this effort defined a 5173 base pair cDNA, shown in FIG. 6, containing a 4214 base pair open reading frame encoding a 156.9 kDa protein. The deduced amino acid sequence of the P2P open reading frame shows a highly basic protein, i.e, pI 9.6, as predicted. Probes to the P2P cDNA detect a single 8 kb mRNA in urine kidney, liver, testes, lung and other tissues and in growing murine 3T3T mesenchymal stem cells. In contrast, P2P mRNA expression is markedly decreased when 3T3T cells undergo the terminal step in the process of adipocyte differentiation. However, P2P mRNA expression is not repressed in nonterminally differentiated adipocytes suggesting that regulation of P2P expression is associated specifically with terminal differentiation.

To establish that the P2P cDNA encodes the P2P subset of hnRNPs, a series of monoclonal antibodies was prepared to a P2P cDNA-derived fusion protein, one of which is designated C130. Other monoclonal antibodies prepared from the P2P cDNA-derived fusion protein are designated C50, C147, and C167. The C130 antibody was shown to detect native 35 to 40 kDa P2Ps and other higher molecular weight products of the P2P cDNA, including a low abundance –160 kDa protein. This protein is recognized by C130 when nuclear extracts are fractionated by single stranded DNA affinity chromatography. This high molecular weight protein is thought to represent the intact product of the P2P cDNA which then appears to be processed into lower molecular weight P2Ps. Since monoclonal antibodies C130 and AC88 both detect P2Ps which are proven hnRNP's of the A/B subtype, this data provides support for the conclusion that the P2P cDNA encodes hnRNP-associated proteins. Data also show that a P2P antisense oligonucleotide selectively represses 30–40 kDa P2P expression.

Studies were next performed to determine if Rb1 might interact with P2P cDNA products. This possibility was suggested by data showing that Rb1 is involved in terminal differentiation and in other growth control mechanisms. Evidence that the P2P cDNA does encode a Rb1 binding protein was obtained by analysis of the Rb1 binding characteristic of GST-P2P fusion proteins. GST-P2P (753 to 909) was specifically shown to bind Rb1. The fact that Rb1 binding to this fusion protein is specifically competed by E1a suggest that the binding occurs to the Rb1 "pocket" domain (28,29). These data are consistent with data concerning the RBQ1 cDNA which was selected based on its ability to bind Rb1 and the fact that the RBQ1 cDNA shows significant homology to the 5' portion of the P2P cDNA (23).

The deduced P2P cDNA product also contains additional interesting domains. The first of these is a cell division sequence motif [CDSM] that has been proposed to be characteristic of proteins involved in the regulation of cell division (27). Examples of proteins that contain this motif include cdc 25, c-myc and several viral proteins including E1a, E7 and SV40 large T antigen. The presence of the CDSM in the P2P cDNA product is consistent with the evidence showing that P2Ps are involved in regulating a cells proliferative potential. Another distinct domain encoded by the 5' portion of the P2P cDNA is a cysteine-rich region that is related to "ring" zinc fingers (30). These zinc finger domains are thought to define protein conformation characteristics that are involved in nucleic acid binding and protein-protein interactions. These attributes are compatible with the fact the P2Ps are known to bind to single stranded DNA and to associate with other hnRNP proteins (31).

These data together suggest that the P2P cDNA can encode protein domains that are important in growth control and that can be modulated by differentiation. The fact that P2P cDNA products can bind Rb1 is highly significant especially since it has been recently shown that both the Rb1 and WT1 tumor suppressor proteins localize to sites of RNA processing as do P2Ps (12,13). Additionally, the ability of Rb1 to bind to nuclear matrix proteins (12,13), such as, p84 (12) and lamin A (32), is of interest since hnRNP particles are also known to be associated with the nuclear matrix (33).

It is therefore considered that the product(s) of the P2P cDNA function to bind tumor suppressors and other cell division regulatory proteins and modulate their function in regulating the processing of RNAs that effect growth control and mediate tumor suppression. Therefore, it is considered that the P2P gene product(s) would represent important regulatory factor(s) that effects many biological and pathological mechanisms including growth control, differentiation, tumor suppression and carcinogenesis.

BRIEF DESCRIPTION OF THE DRAWINGS

FIG. 2 shows P2P cDNA-deduced protein consisting of 1404 amino acids shown in SEQ ID NO:1. A hnRNP-associated domain is encoded by amino acids 853 to 1404 and Rb1 binding domain is encoded by amino acids 753 to 908. Potential nuclear localization signals are present between amino acids 717 to 1323 (underlined) and a cysteine-rich domain resembling a "ring" zinc finger is also present from amino acid 61 to 101 (boxed). The cell division sequence motif (CDSM) from amino acids 79 to 97 (bold) is also shown.

FIGS. 3A–3B show tissue distribution of the P2P mRNA and its specific repression by terminal adipocyte differentiation. FIG. 3A) A murine multiple tissue Northern blot (Clontech) was analyzed using $^{32}$P-labelled random primed P2P cDNA probes under high stringency conditions. Size markers, in kilobases (kb) are shown on the left. FIG. 3B) total cellular RNA (20 mg) isolated from growing undifferentiated 3T3T cells (RG), quiescent serum starved undifferentiated 3T3T cells (Gs), quiescent predifferentiated 3T3T cells arrested 3T3T cells ($G_O/G_D$), nonterminally differentiated 3T3T adipocytes (NTD) and terminally differentiated 3T3T adipocytes (TD) were hybridized with $^{32}$P-labelled random primed P2P cDNA probes under high stringency conditions. A photograph of the ethidium bromide stained gel prior to nucleic acid transfer to the nitrocellulose membrane is shown to indicate equivalent amounts of RNA in each lane.

FIGS. 5A–5B show GST-P2P (753–909) specifically binds Rb1 through the "pocket domain". A) Aliquots of a lysate prepared from K562 cells ($1\times10^7$ cells/sample) were incubated with the glutathione S-transferase leader sequence (GST), or with GST-P2P (1–332), GST-P2P (494–688), GST-P2P (918–1095) or GST-P2P (753–909). As precipitation controls, aliquots of the K562 lysate were immunoprecipitated with anti-Rb1 antibody IF8 or normal rabbit sera. Bound proteins were separated by electrophoresis in a 7% SDS-polyacrylamide gel and transferred to a nitrocellulose membrane. An aliquot of the K-562 crude lysate was included as a positive control for Western analysis. Proteins were visualized by probing the blot with anti-Rb1 antibodies IF-8 or C15. B) Binding of GST-P2P (753–909) to Rb1 is completed by E1a protein. Aliquots of a K562 lysate were incubated as above with GST or GST-P2P (752–909) in the presence (+E1a) or absence (–E1a) of purified adenovirus E1a protein. Bound proteins were separated by electrophoresis in a 7% SDS-polyacrylamide gel and transferred to a nitrocellulose membrane. Proteins were visualized by probing the blot with anti-Rb1 antibodies IF8 or C15.

FIGS. 6A–6F show the nucleotide sequence of the P2P cDNA (SEQ ID NO:2). The nucleotide sequence contains an open reading frame and additional 3' and 5' untranslated regions of the P2P cDNA.

DETAILED DESCRIPTION OF THE INVENTION

Materials and Methods

Cell Lines and Cell Culture Methods

Figure 1:
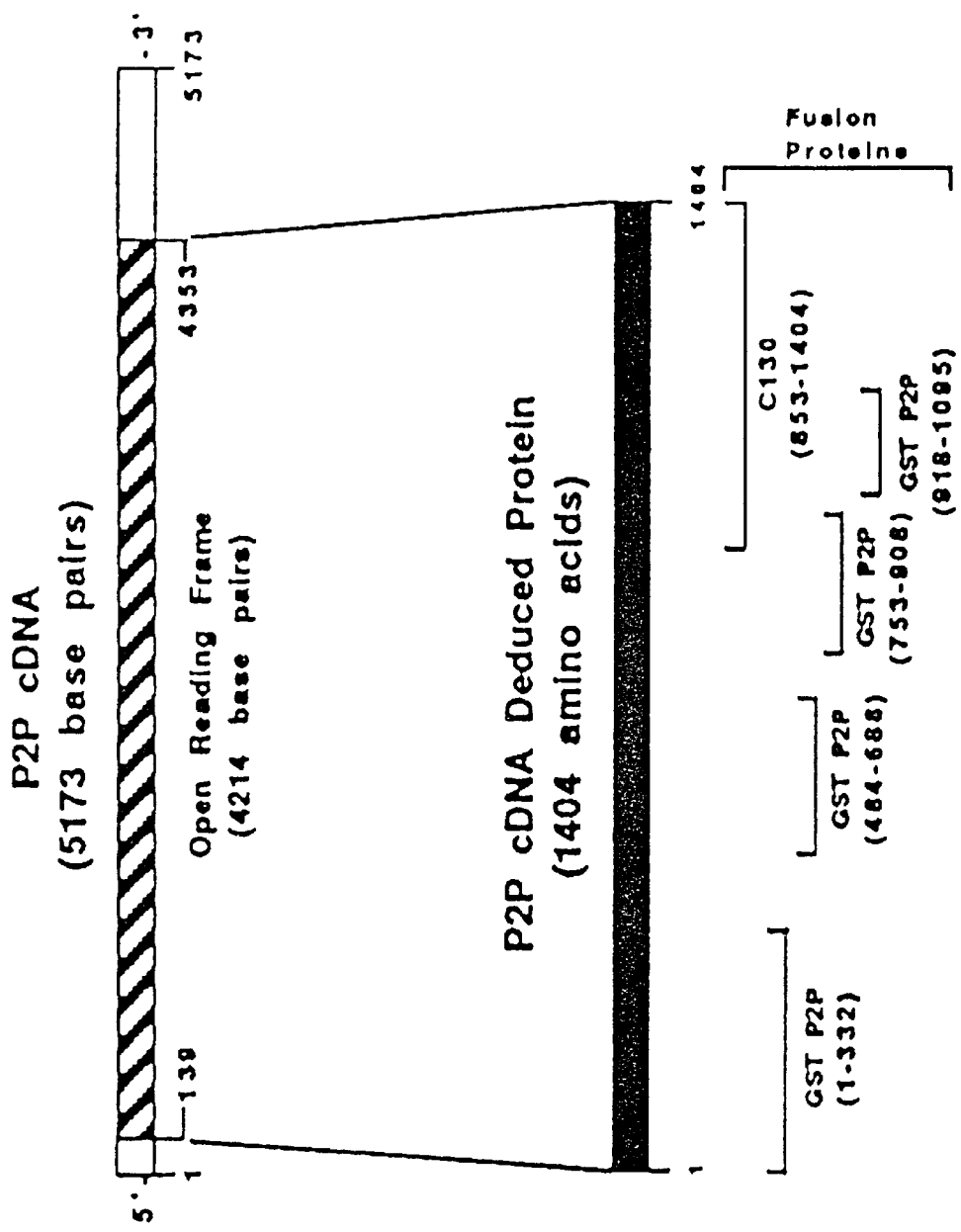
FIG. 1 shows a model for the P2P cDNA and its deduced protein. The P2P cDNA consists of 5173 base pair that contains 4214 base pair open reading frame (ORF) extending from base pair 139 to 4353shown by SEQ ID NO:2. Domains of the deduced 1404 amino acid protein expressed as fusion proteins are also shown. These include four GST-P2P fusion proteins and one b-galactosidase fusion protein designated C130. The amino acid residues of each fusion protein is given parenthetically.

The Balb/c 3T3T mesenchymal stem cell line has been previously described in detail (14). Growing monolayer cultures of these cells are maintained at 37° C. in 5% $CO_2$ in Dulbecco's modified Eagle's medium (DME, Sigma Chemical, St. Louis, Mo.) supplemented with 10% bovine calf serum (BCS, Hyclone, Logan, Utah). To prepare quiescent undifferentiated 3T3T cells they were cultured in DME containing 0.5% BCS for 3 to 4 days at low cell densities of $1\times10^4$ cells/cm$^2$. In some studies, growing undifferentiated cells were treated with 50 mg/ml of P2P antisense or sense oligonucleotides.

The human hematopoietic stem cell line K-562 has also been well characterized (15) and these cells are grown as suspension cultures in RPMI 1640 supplemented with 10% BCS.

Cell Differentiation

The procedures to induce 3T3T cells to undergo differentiation into adipocytes has previously been described (16). This process involves three steps: (a) predifferentiation growth arrest, (b) nonterminal differentiation and (c) terminal differentiation. These steps occur in a parasynchronous manner during a 3–10 day interval after low density, growing cells are cultured in heparinized DME containing 25% human plasma (HP) on ethylene oxide treated petri dishes (16). It is possible to obtain highly enriched populations of cells at each of the differentiation states described above by using well documented modifications of these culture conditions and reagents (1,14,16). These methods were used to prepare cell populations for the current studies Preparation of Cellular Lysates Cellular lysates were prepared as described by Kaelin et al. (17). Growing murine Balb/c 3T3T, and human K562 cells were washed twice with ice-cold PBS, and lysed for 30 minutes at 4° C. in ice-cold EBC buffer (50 mM Tris [PH 8.0], 120 mM NaCl, 0.5% NP-40, 200 mM sodium orthovanadate) containing 10 mg/ml of the protease inhibitors aprotinin, leupeptin, and phenylmethylsulfonyl fluoride (Sigma). The lysates were cleared of nuclei and debris by centrifugation at 14,000× g for 15 minutes at 4° C.

P2P cDNA Cloning a Sequencing

To clone P2P related sequences, approximately 1×10$^6$ plaques front an oligo(dT) random primed lgtl1 murine 3T3 fibroblast cDNA expression library (Clontech, Palo Alto, Calif.) were screened using standard procedures (18) with monoclonal antibody AC88 or FA12. The AC88 antibody, generated against hsp90, cross-reacts with the P2P proteins and has previously been described (19). FA12 also recognizes P2Ps and was prepared against core hnRNP, proteins (20).

Briefly, *E. coli* strain Y1090 was infected with recombinant λgtl1 phage, plated on LB plates and incubated at 42° C. for 3 hours. Subsequently, the plates were overlaid with nitrocellulose filters saturated in 10 mM isopropyl b-D-thiogalactoside (IPTG) and incubated an additional 3 hours at 37° C. to induce the expression of the b-galactosidase fusion proteins. At the end of this period the nitrocellulose filters were air dried for 1 hour at room temperature and subsequently incubated in blocking buffer for 1 hour. Antibody probing was performed at room temperature in the blocking buffer for 2 hours. The filters were washed three times in blocking buffer and probed with an alkaline phosphatase conjugated rabbit anti-mouse IgG (for AC88) or rabbit anti-mouse IgM (for FA12) and the filters developed as previously described (18). AC88 positive clones were further screened with monoclonal antibody FA12. Clones positive for both AC88 and FA12 were identified and isolated by multiple rounds of plaque purification.

The resulting P2P cDNAs were subcloned into the EcoRI site of the pGEM3 vector (Propega, Madison, Wis.) and restriction endonuclease sites were mapped. Various restriction endonuclease fragments of the P2P cDNAs were also subcloned into the vectors Additional 5' P2P sequences were cloned using the Rapid Amplification of cDNA Ends (5' RACE) method (22). For RACE, gene-specific oligonucleotides were used to prime first strand cDNA synthesis from murine 3T3T total RNA using the cDNA Cycle kit (Invitrogen, San Diego, Calif.) and 5'-RACE was performed using a variety of different primer sets. Amplified products were characterized by size analysis, cloned into the pCRII vector (Invitrogen) and their DNA sequences were determined. Throughout this sequencing procedure periodic searches of the DNA databases using the BLAST programs were performed for related sequences. As the sequencing of the 5' end of the P2P cDNA was being completed, one significant homology was discovered. A human cDNA, designated RBQ1 (23), was found to have extensive homology to a 5' region of the murine P2P cDNA. Therefore, primers for the 5' most region of RBQ-1 were also used in characterizing the P2P cDNA using RT-PCR.

RNA Isolation and Northern Analysis

Total cellular RNA was isolated from growing cells, quiescent undifferentiated cells, cells at the nonterminal differentiation state, and terminally differentiated cells. Total cellular RNA (20 mg) from each sample was denatured and fractionated on 1.2% formaldehyde-agarose gels and transferred by blotting to nitrocellulose filters. Blots were pre-hybridized for at least two hours at 42° C. with 5× Denhardts solution, 5× SSC, 50% formamide, 25 mM potassium phosphate, and 100 mg/ml denatured salmon sperm DNA. Hybridizations were carried out overnight at 42° C. in the same solution containing 10% dextran sulfate and random-primed $^{32}$P-labeled P2P cDNA probes. After hybridization the filters were washed and autoradiographed with intensifying screens at −70° C. Tissue specific expression of the P2P mRNA was determined using a mouse multiple tissue Northern blot (Clontech) according to the manufacturer's protocol.

Fusion Protein Expression for Monoclonal Antibody Production

P2P cDNAs were removed from the pGEM vectors using restriction endonuclease Eco RI and ligated downstream from the bacteriophage T7 gene 10 promoter and translation initiation site in the Sco RI site of the pET5a, b and c vectors using standard procedures. Bacterial clones were screened for the presence and orientation of the inserts by digestion with EcoRI and PstI. Individual clones containing the cDNAs in all six possible reading frames were used for subsequent analysis. Expression was achieved using the procedure described by Studier et al (24). For each of the cDNAs only one reading frame, which corresponded to the largest open reading frame, resulted in expression of a fusion protein antigenically related to P$^2$Ps. These fusion proteins were then used to produce an antiP2P specific monoclonal antibody, C130, at the University of Tennessee Memphis Molecular Resource Center Hybridoma Laboratory. Additional monoclonal antibodies, such as those designated C50, C147, and C164 were produced by injection of the transcript product of the P2P cDNA into mice, in the same method as for production of the C130 antibody. Polyclonal antibodies which bind to the P2P transcript are also conceived. The bacterial expression system consisting of the pET5 series of expression vectors, the bacteriophage CE6 and *E. coli* strain HMS174 were gifts from Dr. F. W. Studier.

Expression of P2P-GST and 6X-His-E1a Fusion Proteins

P2P cDNA sequences coding for P2P peptides were generated using RT-PCR and ligated into the pGEX-KG vector to generate the following GST fusion proteins of specific cDNA sequences given parenthetically. GST-P2P (1–332), GST-P2P(494–688), GST-P2P(753–909) and GST-P2P(918–1095). Expression and purification of the GST-fusion proteins was performed as described (25). Fresh overnight cultures of *E. coli* BL21 transformed with either pGEX-KG or one of the above mentioned pGEX-P2P recombinants were diluted 1:10 in LB medium containing 100 mg/ml ampicillin and incubated at 30° C. with shaking for one hour. Fusion protein expression was induced by the addition of IPTG to a final concentration of 0.1 mM and the cultures grown for an additional 3 hours (17). To recover the fusion proteins, the bacterial cultures were sedimented by centrifugation at 5000×g for 5 minutes at 4° C. and resuspended in 1/10 volume of NETN buffer (20 mM Tris [pH 8.0], 100 mM NaCl, 1 mM EDTA, 0.5% NP-40). The cells were lysed on ice by mild sonication and cellular debris was removed by centrifugation at 10,000×g for 5 minutes at 40° C. Glutathione-agarose beads were washed three times and resuspended (1:1 [V/V]) in NETN; bacterial supernatants were then mixed with the glutathione-agarose beads and rocked at 40° C. for one hour to allow the fusion proteins to bind. The beads were finally washed five times with NETN buffer. For analysis of bound bacterial GST- or 6X-His proteins, the beads were boiled in 1× SDS sample buffer, analyzed by SDS polyacrylamide gel electrophoresis and then the proteins were visualized by staining with Coomassie blue.

An E1a vector used to express the E1a protein as a GX-His fusion protein was the gift of Dr. Margaret Quilan, University of Tennessee, Memphis. Expression and purification of the fusion protein was carried out using the His-Bind Kit following the manufacturer's protocol (Novagen, Madison, Wis.).

pRb1-Binding Assay and Immunoprecipitation

Glutathione S-transferase (GST)-P2P fusion proteins were expressed and recovered on glutathione-sepharose beads as described above. Whole-cell lysates of K562 cells ($1 \times 10^7$ cells/sample) were rocked with the beads for 1 hour at 4° C. and then washed five times with NETN buffer. The beads were then boiled in 1× SDS loading buffer and the proteins separated on SDS-polyacrylamide gels and transferred to nitrocellulose membranes. Competition experiments were performed by adding an excess of the 6X-His E1a fusion protein to the cellular lysates prior to the addition of the GST-P2P fusion proteins. The Rb1 protein was visualized by immunoblotting using anti-Rb1 antibodies IF8 or C15 (Santa Cruz Biotechnology, Santa Cruz, Calif.). These antibodies were also used to immunoprecipitate native Rb1 from the cellular lysates to serve as a positive control following the manufacturers' protocol.

Results

Cloning and Characterization of the P2P cDNA

FIGS. 1 and 2 provide a summary of the characteristics of the P2P cDNA that has been cloned. To clone the P2P cDNA, a 3T3 cDNA lgt11 library (Clontech) was screened using the AC88 monoclonal antibody that detects both P2Ps and hsp90 (7,19). AC88 positive clones were rescreened with the monoclonal antibody FA12 against core hnRNP proteins, which was previously shown to also react with the P2Ps (7,20). Two independent clones, designated clone A (1398 bp) and clone B (1943 bp), were found to be recognized by both antibodies. Nucleotide sequencing of the cDNAs showed that the 3' most region of clone A and the 5' most region of clone B were 100% homologous over a 863 base pair region, suggesting that these were overlapping clones derived from a single RNA species. The overlapping clones were joined through a unique Hindlll restriction endonuclease site in the overlapping region to generate 2478 base pair cDNA clone. This includes a 1658 base pair open reading frame and 820 base pair of 3' untranslated sequence.

Additional screens of the cDNA library using this cDNA as the probe failed to give new clones with any additional 5' cDNA sequence. Therefore, the cDNA clone was extended towards the 5' end using RACE (Rapid Amplification of cDNA Ends) methods whereby gene-specific oligonucleotide were used to prime first strand cDNA synthesis from murine 3T3T total RNA and 5'-RACE was performed. Amplified products were cloned and their DNA sequences were determined. This extended the 5' sequence by 1015 base pairs and a GST-P2P fusion protein derived from this region was found to bind Rb1, i.e., GST-P2P (753–909) [FIG. 1].

Throughout the sequencing procedure, periodic searches of the DNA databases using BLAST programs were also performed to search for related sequences especially those encoding Rb1 binding domains. One significant homology was found with a human cDNA, designated RBQ1 (23), which was isolated by its Rb1 binding characteristics. Primers to the 5' end of RBQ1 were therefore used to further extend the P2P cDNA sequence using RT-PCR methods to give a 5173 base pair P2P cDNA.

Analysis of this EDNA reveals a single long open reading frame extending from an ATG codon at base 139 to a termination codon at base 4353. The presence of two in-frame stop codons near the 5' end of the cDNA and several in-frame stop codons at the 3' end of the cDNA suggest that the cDNA contains the entire coding region of the gene. This open reading frame has the potential to code for 1404 amino acids to generate a protein having a predicted molecular mass of 156.9 kDa. The deduced amino acid sequence of the protein is shown in FIG. 2. This highly basic protein (pI, 9.6) has multiple potential nuclear localization signals between amino acids 717 and 1323 which is in agreement with previous findings that P2Ps represent a subset of nuclear hnRNP proteins (7). In addition, computer analysis of the sequence of the P2P cDNA-derived open reading frame shows a unique cysteine-rich domain near the amino terminus (amino acids 61 to 101) which closely resembles the consensus sequence of the "ring" class of $Zn^{++}$ finger domains (26) and another domain near the amino terminus (amino acids 79 to 97) that has been implicated in cell growth control, i.e., the cell division sequence motif [CDSM] (27).

P2P mRNA Expression in Multiple Tissues and Repression by Terminal Adipocyte Differentiation To establish the tissue distribution and the size of the P2P mRNA, a mouse multiple tissue Northern blot was probed with a P2P cDNA probe. A single 8kb mRNA was found in all tissues examined. Very low, but detectable, levels of P2P mRNA were found in kidney, brain, and spleen while moderate levels of P2P mRNA were found in heart, lung, liver and skeletal muscle. The highest levels of P2P mRNA expression were detected in testis (FIG. 3A). The use of probes to different 3' and 5' P2P cDNA domains detected the same 8 kb RNA by Northern blotting (data not shown).

To determine if terminal adipocyte differentiation has an effect on P2P mRNA expression, total RNA was isolated from rapidly growing 3T3T cells, quiescent serum-starved undifferentiated 3T3T cells, quiescent predifferentiated 3T3T cells, nonterminally differentiated 3T3T adipocytes, and terminally differentiated 3T3T adipocytes. Then Northern analysis was used to compare P2P mRNA levels in cells at these states. FIG. 3B shows that the 8 kb P2P mRNA is expressed in all specimens except those derived from cells at the terminal stage of adipocyte differentiation where its expression is markedly repressed. This result is in agreement with previous findings that P2P protein expression is repressed when murine 3T3T mesenchymal stem cells and normal human keratinocytes irreversibly lose their proliferative potential in association with terminal differentiation (7) or senescence (8).

A Monoclonal Antibody Produced Against A P2P cDNA-derived Fusion Protein Reacts With Native P2Ps The carboxy-terminal portion of the P2P cDNA ORF (base pairs 2695 to 4353) were subcloned into the pET5 series expression vector. In this system, the cDNA was placed proximal to the bacteriophage T7 gene 10 translation initiation site such that individual plasmids were isolated containing the cDNA in all six reading frames in phase with the gene 10 protein product. Expression of the protein encoded in each reading frame was obtained by infecting E. Coli strain HMS174 harboring the recombinant plasmid with the bacteriophage CE6 as described above. This bacteriophage is a lambda-derived phage containing the gene for T7 RNA polymerase. Infected bacteria containing the recombinant pET5 vectors produce the T7 RNA polymerase which in turn directs the expression of fusion proteins between the T7 gene 10 protein and the reading frame of the cDNAs. Only one reading frame which corresponds to the 3' end of the large open reading frame [FIG. 1], resulted in expression of fusion proteins antigenically related to P2Ps. The fusion protein was electroeluted from preparative gels and used to produce a P2P-specific monoclonal antibody at the University of Tennessee, Memphis, Molecular Resource Center Hybridoma Laboratory.

Figure 4:
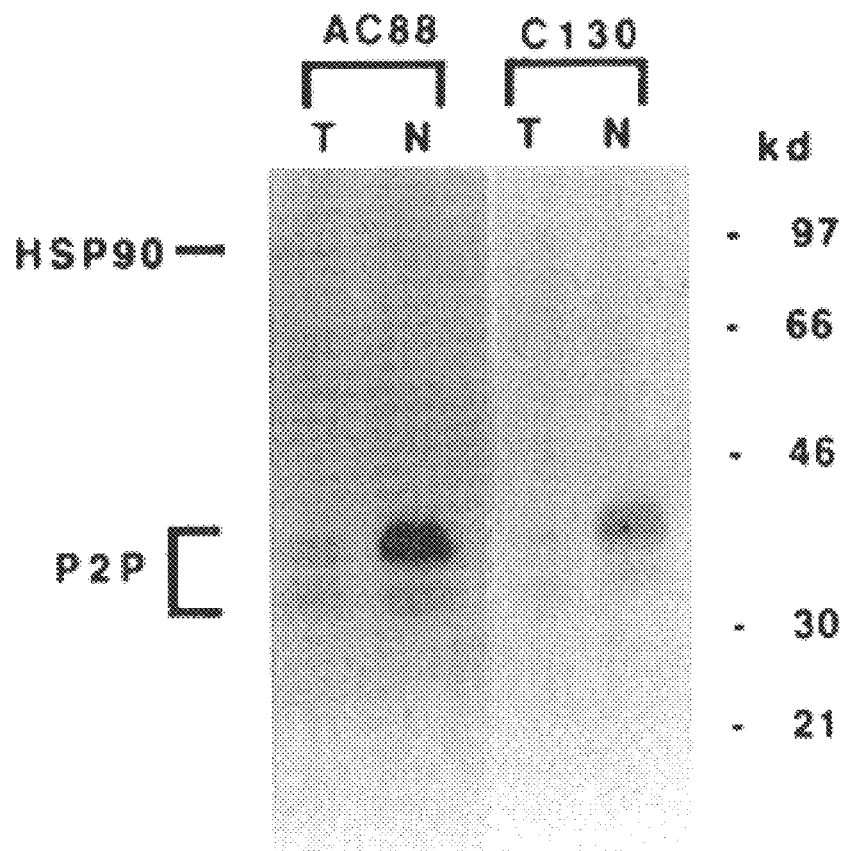
FIG. 4 shows monoclonal antibody C130 derived from a P2P cDNA fusion protein detects native P2P. Rapidly growing undifferentiated murine 3T3T total (T) cellular extracts (100 mg per lane) or nuclear (N) extracts (40 mg per lane) were separated on 10% SDS-PAGE gels and transferred to nitrocellulose membranes. Blots were probed with monoclonal antibody AC88 to detect native P2P proteins or with the P2P cDNA derived monoclonal antibody C130. The location of P2P proteins and heat shock protein 90 (HSP90) are indicated. Size standards are shown in kilodaltons (kd).

One hybridoma so generated was reactive against the purified fusion protein. The antibody, termed C130, was therefore used to probe 3T3T nuclear and total cell extracts by Western analysis. FIG. 4 shows that the C130 monoclonal antibody specifically detects native P2P proteins in a manner similar to the pattern seen with AC88. However, C130 and AC88 recognize separate epitopes because C130 detects only P2Ps whereas AC88 shows cross-reactivity to heat shock protein 90. These data support the conclusion that the cloned P2P cDNA encode hnRNP-related P2P peptides.

Evidence that the P2P cDNA Encodes a Rb1 Binding Peptide Using A P2P-GST Fusion Protein Because Rb1 is required for muscle cell terminal differentiation (10) and data showing that P2P expression is modulated during terminal adipocyte differentiation state, studies were performed to determine if P2P cDNA products might interact with Rb1. To accomplish this GST-P2P fusion proteins were periodically produced to different P2P cDNA domains. Cellular lysates were prepared from human K-562 hematopoietic stem cells which contain abundant Rb1 protein and these lysates were then precipitated with each of the four GST-P2P fusion proteins, i.e. GST-P2P (1–332), (484–688), (753–908) and (918–1095) as illustrated in FIG. 1. The lysates were also precipitated with GST protein alone as a negative control in these experiments. FIG. 5A demonstrates that one fusion protein, GST-P2P (753–909), specifically precipitates a protein that is detected by the anti-Rb1 antibody IF8. FIG. 5a also shows that the GST-P2P (753–909) fusion protein preferentially binds the hypophosphorylated form of Rb-1 which is primarily expressed in the $G_1$ phase of the cell cycle thus suggesting a possible physiological role for the interaction of P2P cDNA products and Rb1 in the control of cell growth.

Most proteins that associate with the hypophosphorylated form of Rb1 bind to a region of Rb1 that has been termed the "pocket" domain (28). To determine if the interaction between Rb1 and GST-P2P (753–909) occurs through the Rb1 "pocket" domain, competition experiments were conducted using purified viral E1a protein. E1a is known to bind specifically to the Rb1 pocket domain and to inhibit cellular proteins from binding to this region (29). FIG. 5B shows that the interaction between the GST-P2P(753–909) fusion protein and Rb1 is blocked by the addition of purified E1a protein. This inhibition is specific for the E1a protein since the addition of another protein, dihydrofolate reductase, did not block the interaction of Rb1 and the GST-P2P fusion protein (data not shown). Therefore, GST-P2P(753–909) binds specifically to the hypophosphorylated form of Rb1 and this interaction occurs through the Rb1 "pocket" domain.

Gene Therapy Using P2P cDNA-Derived Antisense Oligonucleotide Reagents

P2P mRNA and P2P protein is expressed in cells that have proliferative potential regardless of whether they are in a growing or quiescent state. Conversely, the expression of P2P cDNA products is repressed in cells that have lost their proliferative potential as a result of terminal differentiation or senescence. In contrast, transformed cells with malignant characteristics, especially SV40 transformed cells that lack the ability to terminally differentiate or senesce, lack the ability to repress P2P expression. It is conceived, therefore, that the proliferative potential of cancer cells, in general, may be blocked if P2P expression is repressed by the use of antisense oligonucleotide reagents that are targeted to bind to specific domains of the P2P mRNA to block its translation.

The P2P antisense oligonucleotide [5' CAGCAGGAGCT-GTGTT '3 cDNA (3424–3409)] shown by SEQ ID NO:3 and a P2P sense oligonucleotide [5' CTACTAAGC-CATCGGC '3 (3560–3575)] shown by SEQ ID NO:4 have been prepared, isolated, and studied, as shown below in Table I. The antisense oligonucleotides are prepared by Jude Labs (Memphis, Tenn.) and BioSynthesis (Louisville, Tex.). These oligonucleotides (15–50 mg/ml) were added to the culture media of growing 3T3T cells for various times up to 9 days and the effect of these treatments on P2P expression was determined by Western blotting using the AC88 antibody to detect P2Ps.

TABLE 1

Selective Repression of P2P Expression With Antisense Oligonucleotides

|  | Repression of P2P Expression | Repression of Control Protein hsp90 |
| --- | --- | --- |
| P2P Antisense | 83% | 0% |
| P2P Sense | 6% | 0% |

Additional data also suggests that a P2P antisense oligonucleotide can repress cellular proliferation by greater than 50%, whereas a P2P sense oligonucleotide has no effect. Thus, P2P antisense reagents which bind to a domain of the open reading frame of P2P cDNA can be used to repress P2P expression and cellular proliferation, which indicates that the repression of P2P expression may be able to repress the proliferative potential of normal, nontransformed cells, abnormal cells, and cancerous cells both in vitro and in vivo. The results of these studies establish the therapeutic value of P2P antisense reagents for the treatment of proliferative diseases, including cancer.

The monoclonal antibody C130 is commercially available from Santa Cruz Biotechnology under the designation PACT (M56).

THE FOLLOWING REFERENCES ARE INCORPORATED HEREIN BY REFERENCE

1. Scott, R. E., Hoerl, B. J., Wille, J. J., Jr., Florine, D. L., Krawisz, B. R. and Hun, K. (1982) *J. Cell Biol.* 94, 400–405.
2. Tontonoz, P., Erding, H. and Spiegelman, B. M. (1994) *Cell* 79, 1147–1156.
3. Smyth, M. J., Sparks, R. L. and Wharton, W. (1993) *J. Cell Sci.* 106, 1–9.
4. Smas, C. M. and Sul, H. S. (1995) *Biochem. J.* 309, 697–710.
5. McKnight, S. L. (1992) in *Transcriptional Regulation*, eds. McKnight, S. L. and Yamamoto, K. R. (Cold Spring Harbor Laboratory Press, Plainview, N.Y.), pp. 771–795.

6. Wier, M. L. and Scott, R. E. (1986) *Am. J. Pathol.* 125, 546–554.
7. Minoo, P., Sullivan, W., Solomon, L. R., Martin, T. E., Toft, D. O. and Scott, R. E. (1989) *J. Cell Biol.* 109, 1937–1946.
8. Scott, R. E. and Witte, M. M. (1993) *Mol. & Cell. Diff.* 1, 185–195.
9. Dreyfuss, G., Matunis, M. J., Pinol-Roma, S. and Burd, C. G. (1993) *Annu. Rev. Biochem.* 62, 289–321.
10. Schneider, J. W., Gu, W., Zhu, L., Mahdavi, J. and Nadal-Ginard, B. (1994) *Science* 264 1467–1471.
11. Haber, D. A. and Duckler, A. J. (1992) *The New Biologist* 4 97–106.
12. Durfee, T., Mancini, M. A., Jones, D., Elledge, S. J. and Lee, W-H. (1994) *J. Cell Biol.* 127, 609–622.
13. Larsson, S. H., Charlieu, J-P, Miyagawa, K., Endelkamp, D., Rassoulzadegan, M., Ross, A., Cuzin, F., van Heyningen V. and Hastie, N. D. (1995) *Cell* 81, 391–401.
14. Krawisz, B. R. and Scott, R. E. (1982) *J. Cell Biol.* 94, 394–399.
15. Hay, R., Macy, M., Chen, T. R., McClintock, P. and Reid, Y., eds. (1988) in *American Type Culture Collection Catalogue of Cell Lines and Hybridomas, Sixth Edition*, (ATCC Press, Rockville, Md.), p. 134.
16. Wang, H., Sturtevant, D. and Scott, R. E. (1994) in *Cell Biology: A Laboratory Handbook, Vol. I*, ed. Celis, J. E. (Academic Press, Inc., San Diego, Calif.), p. 193–198.
17. Kaelin, W. G., Pallas, D. C., DeCaprio, J. A., Kaye, F. J. and Livingston, D. M. (1991) *Cell* 64, 521–532.
18. Sambrook, Fritsch, E. F., Maniatis, T., eds. (1989) in *Molecular Cloning: A Laboratory Manual, Second Edition*, (Cold Spring Harbor Laboratory Press, Plainview, N.Y.), pp. 12.16–12.24.
19. Toft, D. O., Sullivan, W. P., Smith, D. F., Beito, T. G. and Krco, C. J. (1987) in *Steroid and Steroid Hormone Action*, eds. Spelsberg, T. C. and Kumar, R. (Martinus Nijhoff Publishing, Boston, Mass.) pp. 25–39.
20. Leser, G. P., Escara-Wilke, J. and Martin, T. E. (1984) *J. Biol. Chem.* 259, 1867–1833.
21. Sanger, F., Coulson, A. P., Barrell, B. G., Smith, A. J. M. and Roe, A. (1980) *J. Mol. Biol.* 143, 161–178.
22. Frohman, M. A. (1995) in *PCR Primer: A Laboratory Manual*, eds. Dieffenbach, C. W. and Dveksler, G. A. (Cold Spring Harbor Laboratory Press, Plainview, N.Y.), pp. 381–409.
23. Sakai, Y., Saijo, M., Coelho, K., Kishino, T., Niikawa, N. and Taya, Y. (1995) *Genomics* 30, 98–101.
24. Studier, F. W. and Mofatt, B. A. (1986) *J. Mol. Biol.* 189, 113–130.
25. Guan, K. and Dixon, J. E. (1991) *Analytical Biochem.* 192, 262–267.
26. Freemont, P. S., Hanson, I. M. and Trowsdale, J. (1991) *Cell* 64, 483–484.
27. Figge, J. and Smith, T. F. (1988) *Nature* 334, 109.
28. Fattaey, A. R., Helin, K., Dembski, M. S., Dyson, N., Harlow, E., Vuocolo, G. A., Hanobik, M. G., Haskell, K. M., Oliff, A., Defeo-Jones, D. and Jones, R. E. 1993) *Oncogene* 8, 3149–3156.
29. Paggi, M. G., Martelli, F., Fancuilli, M., Felsani, A., Sciacchitano, S., Varmi, M., Bruno, T., Carapella, C. M. and Floridi, A. (1994) *Cancer Res.* 54, 1098–1104.
30. Berg, J. M. and Shi, Y. (1996) *Science* 271, 1081–1085.
31. Minoo, P., Martin, T. E. and Riehl, R. M. (1991) *Biochem and Biophys Res. Comm.* 176, 747–755.
32. Ozaki, T., Saijo, M., Murakami, K., Enomoto, H., Taya, Y. and Sakiyama, S. (1994) *Oncogene* 9, 2649–2653.
33. He, D., Martin, T. and Penman, S. (1991) *Proc. Natl. Acad. Sci. USA* 88, 7469–7473.
34. The Twelfth Bienniel Conference of the International Cell Cycle Society (1988) *Cell Tissue Kinet.* 21, 205–212.
35. Slamon, D. J., and Souza, L. M., U.S. Pat. No. 4,918,162 (1990).
36. Silvestrini, R., U.S. Pat. No. 4,960,709 (1990).

What is claimed is:

1. An isolated DNA molecule comprising SEQ ID NO:2.
2. The DNA sequence of claim 1 with its complementary strand.
3. The DNA molecule of claim 1 which hybridizes under stringent conditions to a transcript of approximately 8 kilobases in murine liver, kidney, testes, lung and in murine 3T3T stem cells.
4. The DNA molecule of claim 1 which is not expressed in terminally differentiated 3T3T cells or in senescent human keratinocytes.
5. The DNA molecule of claim 1 which comprises an open reading frame of at least 4814 nucleotides.
6. The DNA molecule of claim 1 which encodes the P2P polypeptide.
7. The DNA molecule of claim 1 which is mouse DNA.

8. An isolated ribonucleic acid molecule comprising a transcript encoding a P2P protein comprising the amino acid sequence of SEQ ID No. 1.

9. An isolated antisense oligonucleotide which anneals to a complementary portion of a mRNA transcript comprising SEQ ID No. 2, wherein binding of said antisense oligonucleotide to said mRNA transcript represses expression of P2P gene.

10. The antisense oligonucleotide of claim 9, wherein said antisense oligonucleotide anneals to an open reading frame of said mRNA transcript under physiological conditions.

11. The antisense oligonucleotide of claim 5, wherein said antisense oligonucleotide is complementary to an open reading frame of said mRNA transcript encoding a P2P protein having an amino acid sequence of SEQ ID No. 1.

12. The antisense oligonucleotide of claim 9 SEQ ID NO:3.

13. A method of inhibiting the expression of a gene encoding a P2P protein, comprising the step of:

contacting growing cells selected from the group consisting of normal, abnormal, and cancer cells with the antisense oligonucleotide of claim 9.

14. The method of claim 13 wherein the antisense oligonucleotide comprises SEQ ID NO:3.

15. A method for repressing the proliferative potential of a cell, comprising the step of:

contacting growing cells selected from the group consisting of normal, abnormal, and cancer cells with the antisense oligonucleotide of claim 9, wherein inhibition of the expression of P2P gene by said antisense oligonucleotide represses the proliferative potential of said cell.

16. The method of claim 15 wherein the antisense oligonucleotide comprises SEQ ID NO:3.

17. A method for inhibiting the translation of a P2P mRNA transcript in cells, comprising the step of:

contacting cells selected from the group consisting of normal, abnormal, and cancer cells with the antisense oligonucleotide of claim 9, wherein said antisense oligonucleotide anneals to the portion of the P2P mRNA transcript encoding a C-terminal region of the P2P protein comprising the domain that binds to RNA.

18. The method of claim 17 wherein said antisense oligonucleotide anneals to the portion of the P2P mRNA encoding one or more of epitopes recognized by antibodies selected from the group consisting of C130, FA12 and AC88.

19. The method of claim 17 wherein said antisense oligonucleotide comprises SEQ ID NO: 3.

* * * * *